(12) United States Patent
Lefeber et al.

(10) Patent No.: US 9,759,704 B2
(45) Date of Patent: Sep. 12, 2017

(54) DEVICE AND PROCESS FOR OIL QUALITY MONITORING BASED ON LIGHT WAVES

(71) Applicant: Waukesha Electric Systems, Inc., Waukesha, WI (US)

(72) Inventors: Paul Lefeber, Fanklin, WI (US); Jeffrey J. Nemec, Oconomowoc, WI (US)

(73) Assignee: SPX Transformer Solutions, Inc., Waukesha, WI (US)

( * ) Notice: Subject to any disclaimer, the term of this patent is extended or adjusted under 35 U.S.C. 154(b) by 47 days.

(21) Appl. No.: 14/846,163

(22) Filed: Sep. 4, 2015

(65) Prior Publication Data

US 2016/0069852 A1  Mar. 10, 2016

Related U.S. Application Data

(60) Provisional application No. 62/045,899, filed on Sep. 4, 2014.

(51) Int. Cl.
*G01N 21/85*  (2006.01)
*G01N 33/03*  (2006.01)
*G01N 21/94*  (2006.01)

(52) U.S. Cl.
CPC ............. *G01N 33/03* (2013.01); *G01N 21/94* (2013.01); *G01N 2201/062* (2013.01); *G01N 2201/08* (2013.01)

(58) Field of Classification Search
CPC .... G01N 33/2888; G01N 33/03; G01N 21/51; G01N 33/2847; G01N 33/2835; G01N 33/30
USPC ......................................... 250/573, 576, 221
See application file for complete search history.

(56) References Cited

U.S. PATENT DOCUMENTS

| | | | | |
|---|---|---|---|---|
| 3,384,885 A | * | 5/1968 | Forbush | G01F 23/2927 250/577 |
| 6,519,034 B1 | * | 2/2003 | Engler | G01N 21/532 250/574 |
| 7,172,903 B2 | * | 2/2007 | Schilowitz | G01N 21/3151 250/343 |

* cited by examiner

*Primary Examiner* — Que T Le
(74) *Attorney, Agent, or Firm* — Baker & Hostetler LLP

(57) ABSTRACT

A system and a process for detecting oil quality includes a light source configured to generate light within an oil container and a sensor configured to detect light from the light source after it has traversed through the oil in the oil container and generate an output signal. The system and process further includes a monitor configured to receive the output signal from the sensor and determine an oil quality of an oil in the oil container.

20 Claims, 7 Drawing Sheets

DEVICE AND PROCESS FOR OIL QUALITY MONITORING BASED ON LIGHT WAVES

CROSS REFERENCE TO PRIOR APPLICATIONS

This application claims the benefit from U.S. Provisional Application No. 62/045,899 filed on Sep. 4, 2014, which is hereby incorporated by reference for all purposes as if fully set forth herein.

FIELD OF THE INVENTION

The invention relates to a device and process for monitoring oil quality. In particular, the invention relates to a device and process for monitoring oil quality to detect and communicate early stage problems in oil.

BACKGROUND OF THE INVENTION

The quality of oil is critical in a number of different applications including industrial applications, food related applications, and the like. Typically, in order to determine oil quality, one has to obtain a sample of the oil and thereafter analyze the oil in a laboratory setting to determine the quality thereof.

For example, dielectric insulating oil is utilized in many electrical devices such as power transformers, load tap changers (LTCs), circuit breakers and voltage regulators. For example, the use of vacuum interruption during switching using LTCs began a few decades ago and its use is increasing with greater customer acceptance. The two primary suppliers of vacuum LTCs utilize preventative autotransformer (reactor) switching principle with vacuum interrupters to accomplish the tap change. The problem with this method of switching is that failure of the vacuum interrupter can lead to property damage and/or personal injury. However, the failure of the vacuum interruption system in other LTCs does not result in an immediate failure. This is due to a different switching technology. One such LTC was tested and continued to operate with arcing in oil for more than 20,000 operations. Nevertheless, even these LTCs will typically eventually fail. With constantly decreasing budgets, utilities are faced with the need to extend maintenance cycles which require de-energized internal inspections while not reducing the reliability. These internal inspections are costly and time-consuming.

Similarly, many food grade oils are stored and subsequently utilized in food preparation. However, the food grade oils sometime become contaminated or spoiled. This results in subsequent contamination or spoilage of the resulting food product.

Accordingly, there is a need for a system and process to more accurately, quickly, and more cost-effectively detect early-stage problems with oil products utilizing new monitoring systems.

SUMMARY OF THE INVENTION

The foregoing needs are met, to a great extent, by the invention, wherein in one aspect a technique and apparatus are provided that provides a system and process to detect early-stage issues associated with oil quality utilizing.

In accordance with one aspect, a system for detecting oil quality includes a light source configured to generate light within an oil container, a sensor configured to detect light from the light source after it has traversed through oil in the oil container and generate an output signal, a monitor configured to receive the output signal from the sensor and determine the oil quality of the oil in the oil container.

The light source may be arranged in the oil container. The sensor may be arranged in the oil container. The system may further include a contact to receive and reflect the light from the light source to the light sensor. The system may further include a fiber optic cable to guide the light from the light source into the oil container. The system may further include a fiber optic cable to guide the light received from the light source from the oil container to the sensor. The monitor may include a communication device configured to communicate at least one of data, a status, problems, location of the oil, recommended next steps and additional testing based on the determined oil quality.

In accordance with another aspect, a process for detecting oil quality includes generating light within an oil container with a light source, detecting the light from the light source after it has traversed through the oil in the oil container and generating an output signal with a sensor, monitoring the output signal from the sensor and determining an oil quality of an oil in the oil container.

The light source may be arranged in the oil container. The sensor may be arranged in the oil container. The process may further include arranging a contact to receive and reflect the light from the light source to the light sensor. The process may further include arranging a fiber optic cable to guide the light from the light source into the oil container. The process may further include arranging a fiber optic cable to guide the light received from the light source from the oil container to the sensor. The process may further include communicating at least one of data, a status, problems, recommended next steps and additional testing based on the determined oil quality.

There has thus been outlined, rather broadly, certain aspects of the invention in order that the detailed description thereof herein may be better understood, and in order that the present contribution to the art may be better appreciated. There are, of course, additional aspects of the invention that will be described below and which will form the subject matter of the claims appended hereto.

In this respect, before explaining at least one aspect of the invention in detail, it is to be understood that the invention is not limited in its application to the details of construction and to the arrangements of the components set forth in the following description or illustrated in the drawings. The invention is capable of aspects in addition to those described and of being practiced and carried out in various ways. Also, it is to be understood that the phraseology and terminology employed herein, as well as the abstract, are for the purpose of description and should not be regarded as limiting.

As such, those skilled in the art will appreciate that the conception upon which this disclosure is based may readily be utilized as a basis for the designing of other structures, methods and systems for carrying out the several purposes of the invention. It is important, therefore, that the claims be regarded as including such equivalent constructions insofar as they do not depart from the spirit and scope of the invention.

DETAILED DESCRIPTION

Figure 1:
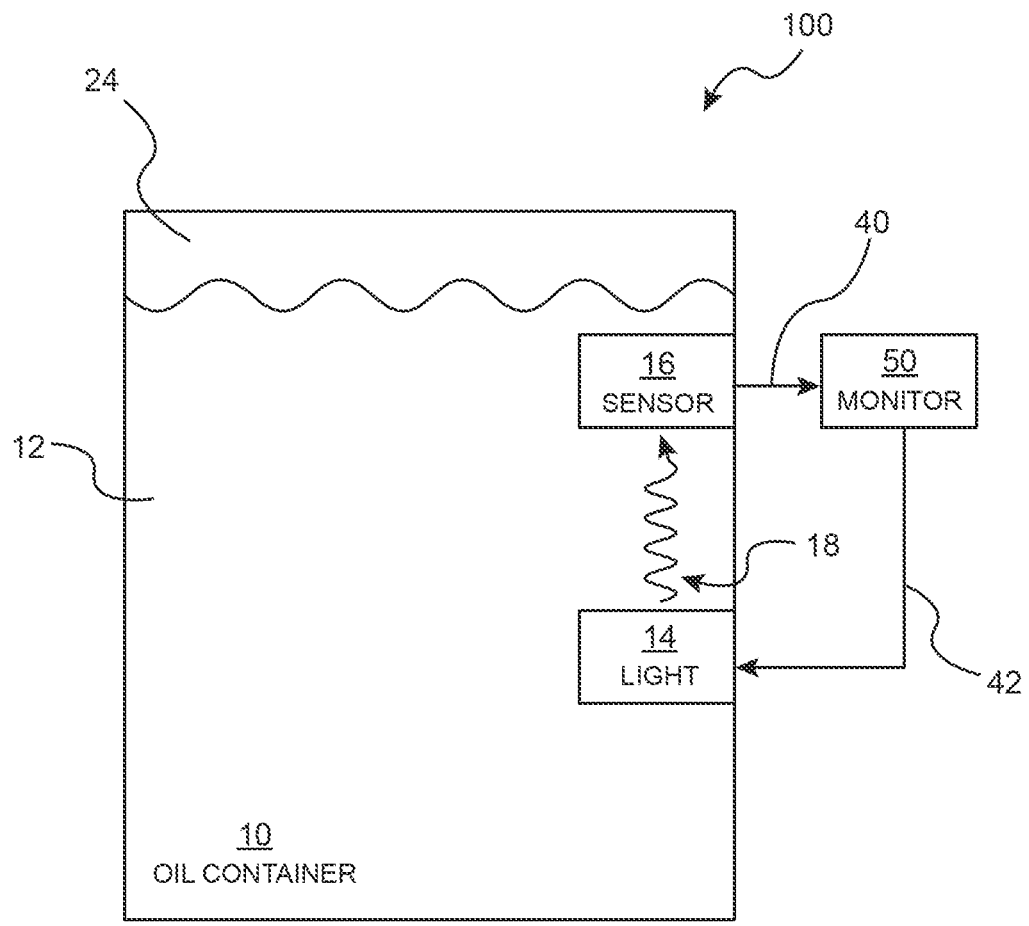
FIG. 1 shows one aspect of an analysis system in accordance with the invention.

The invention will now be described with reference to the drawing figures, in which like reference numerals refer to like parts throughout. Aspects of the invention advantageously provide a system and process to detect early-stage issues with electrical components.

Electrical components may be filled with a fluid that serves several purposes. The fluid acts as a dielectric media, an insulator, and/or as a heat transfer agent. The fluid used in electrical components may be a mineral oil. Other types of fluids may include askerals, silicone type fluids, natural esters, and the like, hereinafter generically referred to as an insulating oil. The insulating oil may be in contact with numerous internal parts of the electrical component and monitoring oil quality can reveal the faults, precursors of developing faults, or other issues with the electrical components that are a result of the natural aging processes of the oil.

Thermal faults may be detected by the presence of by-products of solid insulation decomposition; insulation overheating as a result of the electrical component generating more heat and deteriorating the insulation; insulation liquid overheating which results in breakdown of liquid by heat and formation of high thermal gases; corona discharge; arcing within the electrical component, formation of acids, complex oxides, and the like.

This invention includes use of oil monitoring of electrical components, such as free breathing LTCs, which are external to, and part of some power transformers and/or oil circuit breakers, voltage regulators, and other oil filled electrical equipment. This invention includes use of oil monitoring of other types of oil filled machines including engines, transmissions, gearboxes, and the like. For example monitoring the oil quality in a gearbox of a wind turbine.

The device and process may be used to identify the potential for or the early stages of contact filming, heating, sludge formation, and/or the like and assess the condition of the electrical component, such as a LTC, without performing an internal inspection. The monitoring can identify electrical components, such as LTCs, in early stages of failure before damage to the electrical components or failure can occur.

Additionally, food grade oil may be subject to spoilage or contamination over time. The device and process of the invention may be utilized to identify the potential for or the early stages of spoilage or contamination. This avoids use of spoiled oil, assist users with timely reordering of oil, and the like. Moreover, although oil quality is discussed herein, the quality of other fluids may be determined in a similar manner within the scope of the invention.

FIG. 1 shows an analysis system in accordance with the invention. In particular, FIG. 1 shows an oil container 10 having an oil 12 to be analyzed by an analysis system 100. The analysis system 100 may include a light source 14 and a sensor 16 to sample the oil from the oil container 10 from time to time as determined by the analysis system 100. The oil container 10 may further include an airspace 24. The analysis system 100 further includes a monitor 50.

The light source 14 may emit a light 18. The light source 14 may include one or more lights of a single or various colors. The light source may be generated by one or more LEDs, one or more incandescent light sources, one or more fluorescent light sources, and the like. The light 18 may be received by the sensor 16. A light intensity received by the sensor 16 may be converted to a signal value and sent to the monitor 50. The signal value may be correlated to provide values for good, acceptable, or poor quality of the oil 12.

The light source 14 may be configured to emit various colors to be received by the sensor 16 to determine oil quality and/or an actual cause of deteriorating oil quality. Different light colors may be required for different oils. Moreover, the sensor 16 may detect other physical changes in the light 18 as the light traverses the oil 12. The physical changes in the light 18 being indicative of the oil quality, the source of a change in oil quality, the moisture amount, particles in the oil, and the products indicative of arcing, heating, spoilage, contamination and/or the like.

The sensor 16 may be a multispectral sensor. For example, the sensor 16 may be a multispectral sensor utilizing on-chip filtering to pack eight wavelength selective photodiodes onto an array. The sensor 16 may be a multi-spectral sensor provided by PIXELTEQ, Largo Fla., USA. It is contemplated that the sensor 16 may be implemented in a number of other different ways as well.

In the arrangement of FIG. 1, the sensor 16 may be arranged in the oil container 10 and the light source 14 may also be arranged within the oil container 10. The analysis system 100 may include a communication line 42 from the monitor 50 to control and power the light source 14. The analysis system 100 may further include a communication line 40 providing output from the sensor 16 to the monitor 50. In this arrangement, the light 18 from the light source 14 may be directed through the oil 12 toward the sensor 16 for direct reception thereof.

The analysis system 100 may determine and monitor the condition of the oil 12 from the oil container 10 on an hourly basis, a daily basis, a weekly basis, in an ad hoc manner, periodically, or the like. Further details of the monitoring process are described below.

Figure 2:
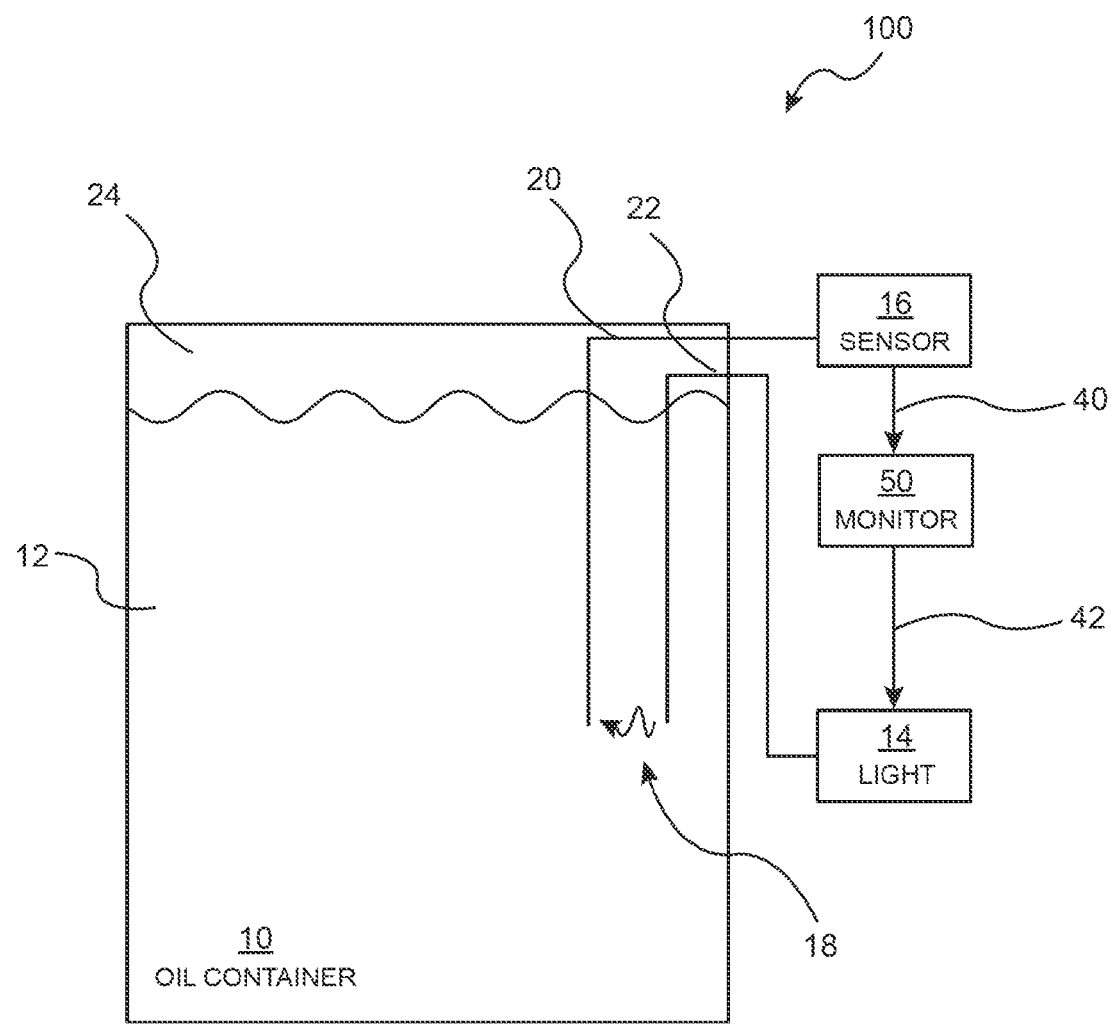
FIG. 2 shows another aspect of an analysis system in accordance with the invention.

FIG. 2 shows another aspect of the analysis system in accordance with the invention. In particular, in the aspect shown in FIG. 2, the sensor 16 may be arranged outside the oil container 10. Likewise the light source 14 may also be arranged outside of the oil container 10. Sensor input to the sensor 16 may be through a fiber-optic cable 20. Light generation may be provided by the light source 14 which is output to another fiber-optic cable 22. Within the oil container 10, the fiber-optic cable 22 may emit light 18 from an output end thereof to be received by an input end of the fiber-optic cable 20. Accordingly, this arrangement benefits from the sensor 16 and the light source 14 being arranged external to the oil container 10 reducing the possibility of damage to the light source 14 and sensor 16 by oil. Moreover, this arrangement prevents the light source 14 and the sensor 16 from contaminating the oil 12. Finally, maintenance on the analysis system 100 may be easier to perform with this arrangement.

Figure 3:
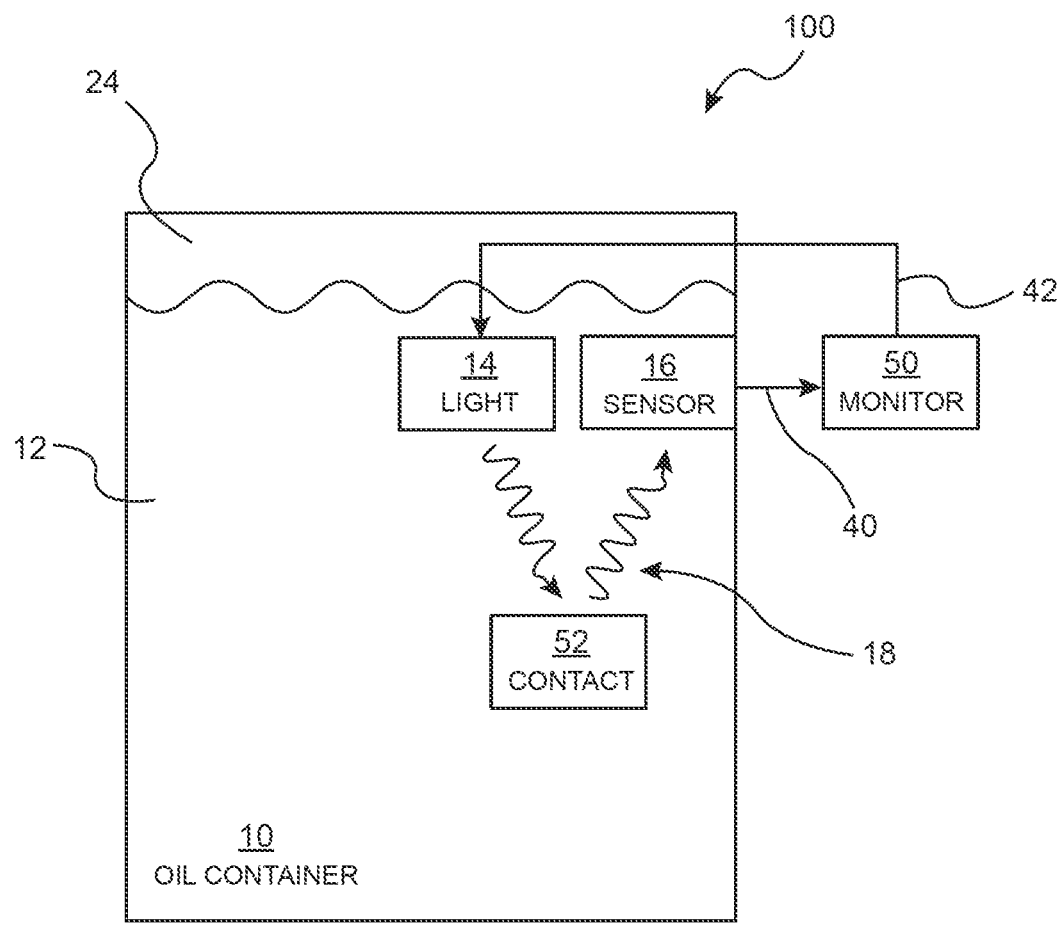
FIG. 3 shows yet another aspect of an analysis system in accordance with the invention.

FIG. 3 shows yet another aspect of the analysis system in accordance with the invention. In the arrangement of FIG. 3, the sensor 16 may be arranged in the oil container 10 and the light source 14 may also be arranged within the oil container 10. The analysis system 100 may include a communication line 42 from the monitor 50 to control and power the light source 14. The analysis system 100 may further include a communication line 40 providing input to the sensor 16 to the monitor 50.

In the arrangement of FIG. 3, the light 18 may be emitted from the light source 14 toward a contact 52. The contact 52 may reflect the light 18 to the sensor 16. The contact may have various physical properties to provide reflection of the light from the light source 14 to the sensor 16. The physical properties may be changed based on the quality of the oil 12 within the oil container 10. For example, the contact 52 may provide an indication of oil quality based on a film buildup on the surface thereof. In this regard, a new contact 52 would reflect more light than a contact 52 that has been tarnished by buildup of oil impurities that are a result of a tarnished surface. In one aspect, the contact 52 may be silver plated. Additionally, the physical properties of the oil 12 may also alter the physical properties of the light as it traverses the oil 12.

Figure 4:
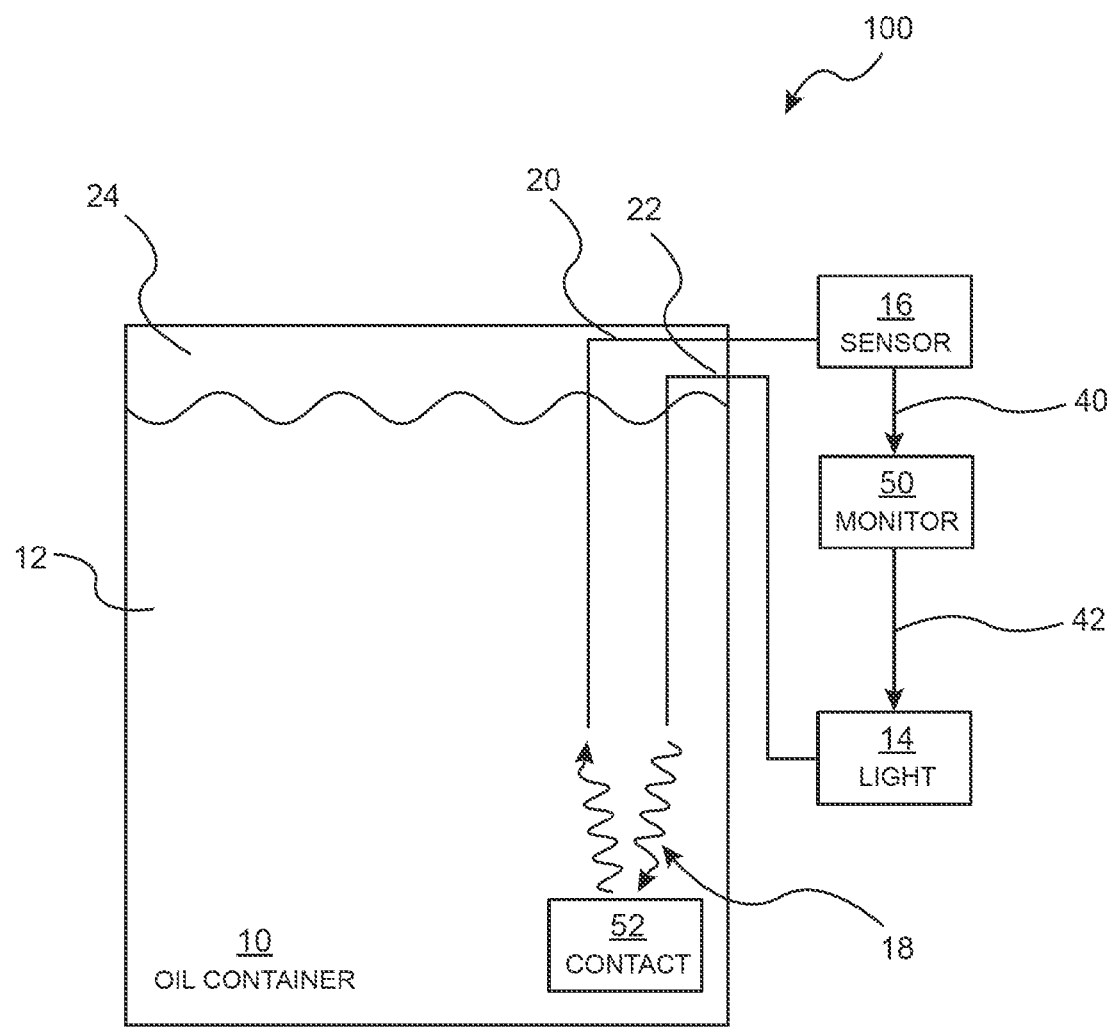
FIG. 4 shows another aspect of an analysis system in accordance with the invention.

FIG. 4 shows another aspect of an analysis system in accordance with the invention. In particular, in the aspect shown in FIG. 4, the sensor 16 may be arranged outside the oil container 10. Likewise the light source 14 may also be arranged outside of the oil container 10. Sensor input to the sensor 16 may be through a fiber-optic cable 20. Light generation may be provided by the light source 14 which is output to another fiber-optic cable 22. Within the oil container 10, the fiber-optic cable 22 may emit light from an output end thereof to be reflected against the contact 52 and received by an input end of the fiber-optic cable 20. Accordingly, this arrangement benefits from the sensor 16 and light source 14 being arranged external to the oil container 10 reducing the possibility of damage to the light source 14 and the sensor 16 by the oil 12. Moreover, this arrangement prevents the light source 14 and the sensor 16 from contaminating the oil 12. Finally, maintenance on the analysis system 100 may be easier to perform with this arrangement.

Figure 5:
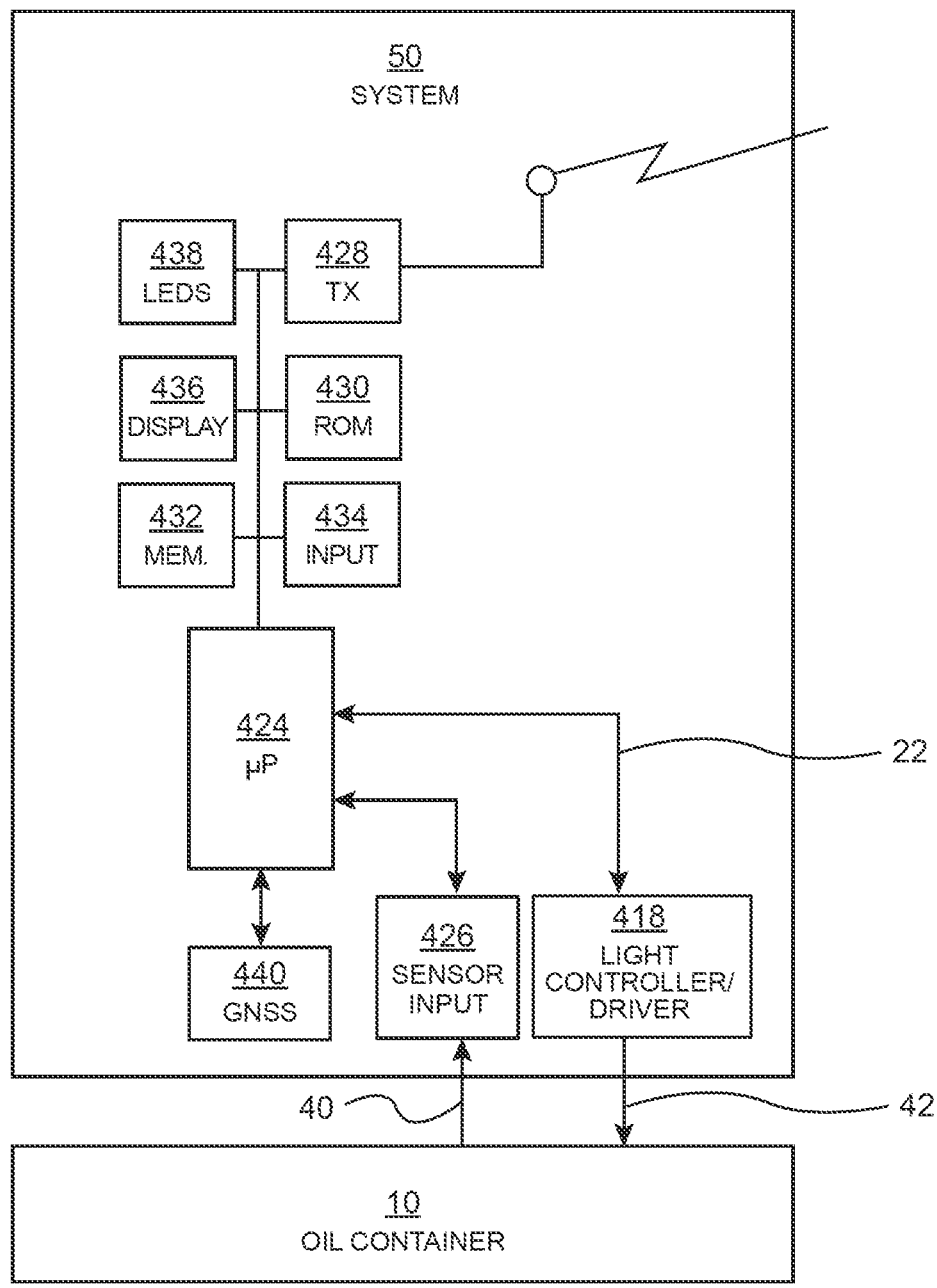
FIG. 5 shows a monitoring device in accordance with the invention.

FIG. 5 shows a monitoring device in accordance with one aspect of the invention. The monitor 50 may include a memory 432 to store an operating system together with one or more applications for analyzing the oil quality based on the light 18 received from the sensor 16. The memory 432 may further include the ability to store analysis, data for trending over time, and the like as needed for the monitoring.

The monitor 50 may further include a read-only memory 430 to provide the basic memory functionality such as the storage of firmware or the like. The monitor 50 may further include a display 436, such as a LCD display, LED display, or the like, to provide a user or maintenance personnel with information, data, various operating details, and the like of the monitor 50. The monitor 50 may further include an input device 434 such as a keyboard, keypad, USB connector, mouse input, FireWire input, or the like for providing input to the monitor 50 or the microprocessor 424. The monitor 50 may further include various operating lights, such as LEDs 438, to indicate the operating condition of the monitor 50, communication status of the monitor 50, power status of the monitor 50, or the like.

The monitor 50 may further include a transmitter 428. The transmitter 428 may use a communication channel as defined herein such as a wireless fidelity protocol communication channel, cellular data protocol communication channel, or the like to transmit various statuses, data, alarms, location of the oil, and conditions of the monitor 50. Of course the transmitter 428 may include a hardwired connection instead of or in addition to the wireless connections. The transmitter 428 may include additional structure in order to provide transmission capability including a universal asynchronous receiver transmit circuit, RS-232 and the like. Additionally, the transmitter 428 may transmit the results of the oil quality analysis performed by the microprocessor 424.

The monitor 50 may further include a light controller/driver 418. The light controller/driver 418 may connect to the light source 14 via communication line 42 to drive the light source 14 as desired. The communication line 42 may further provide power to the light source 14 as needed.

The monitor 50 may further include a sensor input 426. The sensor input 426 may receive input from the sensor 16 and forward the sensor input to the monitor 50 and may further provide the sensor input to the microprocessor 424. The sensor input 426 may include any other additional circuitry to filter and manipulate the sensor 16 output for use by the monitor 50. For example, the sensor input 426 may include an analog to digital converter. The monitor 50 may further include a global navigation satellite system (GNSS) 440 that may include a device and/or system that may estimate a location of the monitor 50 and/or the oil container 10.

Figure 6:
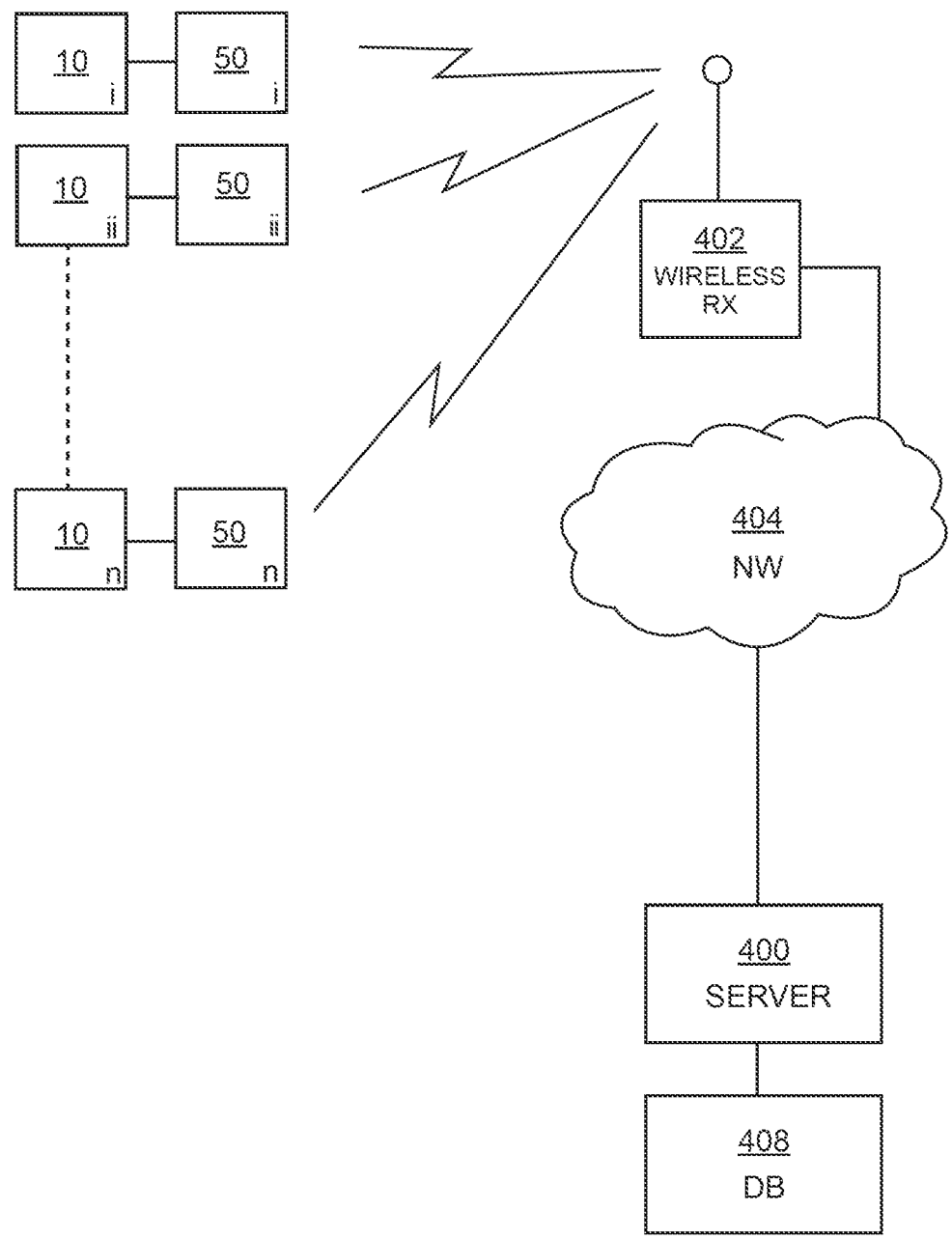
FIG. 6 shows a system for monitoring a plurality of analysis systems.

FIG. 6 shows a system for monitoring a plurality of analysis systems. In particular, FIG. 6 shows a series of oil containers 10(i-n) and monitors 50(i-n) monitoring the oil within oil a plurality of containers 10. The monitors 50 may each include a transmitter 428 as described above. The transmitter 428 may communicate with a transmitter 402 along a communication channel as defined herein, such as a wireless access point using a wireless fidelity protocol, a cellular data transmitter, or the like, to receive data from each of the monitors 50 of FIG. 6. The data may then be placed on a network 404 such as a wireless network, the Internet, intranet, cloud storage, or the like to transmit the data to a computer generically referred to herein as a server 400. The server 400 may subsequently store the data in a database 408. The server 400 and database 408 may monitor the data and generate alarms and/or reports regarding the condition of the oil in each of oil containers 10, the status of the monitors 50, recommend further testing, or the need to perform maintenance, or the like. Additionally, the above described functionalities of the microprocessor 424 and the server 400 may be handled exclusively by either or shared in different ways.

Figure 7:
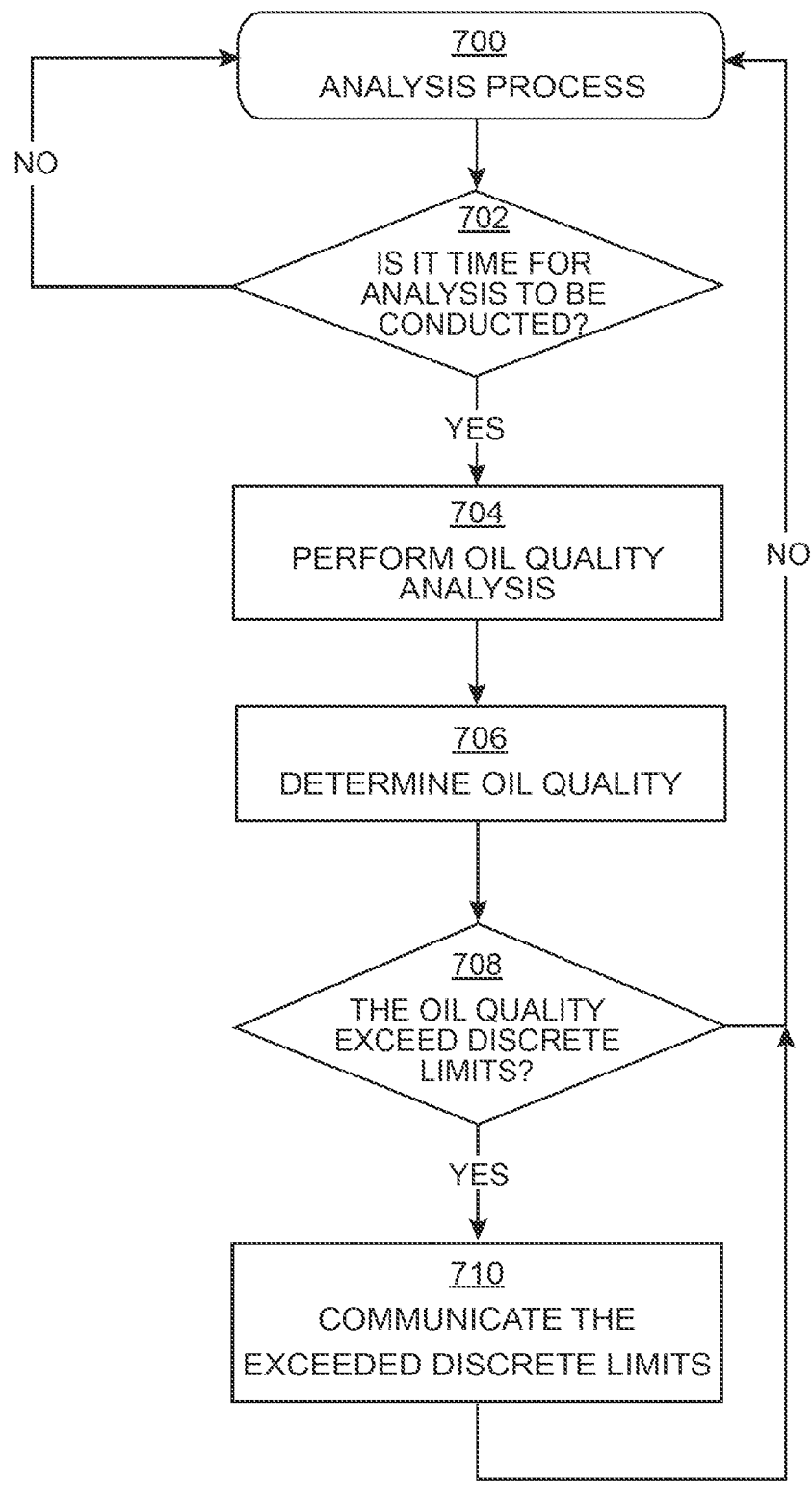
FIG. 7 shows a process of analyzing in accordance with one aspect of the invention.

FIG. 7 shows a process of analyzing oil in accordance with the invention. In particular, FIG. 7 shows an analysis process 700 that may be executed by the monitor 50 and/or the server 400. In particular, the microprocessor 424 may take active steps to execute the process as described in conjunction with FIG. 7.

The process may be performed continuously or discreetly. In this regard, the process 700 may execute hourly, daily, weekly, or periodically using any timeframe. The process 700 may also execute in an ad hoc manner as requested by a user or in response to prior executions of the process 700. For example, if the analysis is indicating results that are unfavorable, the process 700 may be executed more frequently in the future.

As shown in 702, the process 700 determines whether it is time for analysis to be conducted. If no, the process 700 may simply loop and wait until it is time to execute the process 700. If yes, the process 700 may advance to perform the oil analysis. It is within the scope and spirit of the invention that the order of the process 700 may be changed, not all the steps need to be performed, and additional steps may be included.

Next, the process 700 performs oil quality monitoring as shown in 704. In this regard, the monitor 50 may control the light source 14 to emit light 18. Thereafter the monitor 50 may control the sensor 16 to receive light 18 from the light source 14.

In process 706, the light 18 received by the sensor 16 may be processed by the monitor 50 to determine moisture, oil quality, particles, spoilage, contamination and the like based on the received light 18.

As shown in 708, when the oil quality is acceptable as shown in 708, the analysis process 700 may end and loop back to the beginning of the process and await the next time the analysis process is to be conducted. On the other hand, if the oil quality as shown in 708, the process will move to 710 and communicate that the oil quality is unacceptable, possible recommendations for further testing to confirm equipment condition, and/or for planning for future scheduled maintenance. The communication of the data may be to the display 436 of the monitor 50, to the LEDs 438 of the monitor 50, may be transmitted by the transmitter 428 of the monitor 50 and/or the like. Alternatively, the process 700 may be conducted in the server 400 with the data required being transmitted from the monitor 50 by the transmitter 428. The communication may further be forwarded to any user, computer, or entity as desired via e-mail, SMS text message, Web application, or the like. Such communication may include any of the aforementioned data, location of the oil, status, location of the oil, alarms, next steps, recommendations, or the like.

Accordingly, use of this invention will provide a means for very early detection of oil quality, potential failures and/or identification of electrical components trending towards failure and in need of maintenance. Detection of such issues in LTCs long before damage can occur saves extensive repair costs and emergency (unplanned) outages. In addition this will facilitate better utilization of electrical components for customers. Moreover, detection of for all quality as it relates to food products may prevent poor subsequent food quality.

The invention may include communication channels that may be any type of wired or wireless electronic communications network, such as, e.g., a wired/wireless local area network (LAN), a wired/wireless personal area network (PAN), a radiofrequency identification device (RFID), mesh network, wired/wireless home area network (HAN), a wired/wireless wide area network (WAN), a campus network, a metropolitan network, an enterprise private network, a virtual private network (VPN), an internetwork, a backbone network (BBN), a global area network (GAN), the Internet, an intranet, an extranet, an overlay network, a cellular telephone network, a Personal Communications Service (PCS), using known protocols such as the Global System for Mobile Communications (GSM), CDMA (Code-Division Multiple Access), W-CDMA (Wideband Code-Division Multiple Access), Wireless Fidelity (Wi-Fi), Bluetooth, Long Term Evolution (LTE), EVolution-Data Optimized (EVDO) and/or the like, and/or a combination of two or more thereof.

The invention may be implemented in any type of computing devices, such as, e.g., a desktop computer, personal computer, a laptop/mobile computer, a personal data assistant (PDA), a mobile phone, a tablet computer, cloud computing device, and the like, with wired/wireless communications capabilities via the communication channels.

Further in accordance with various aspects of the invention, the methods described herein are intended for operation with dedicated hardware implementations including, but not limited to, PCs, PDAs, semiconductors, application specific integrated circuits (ASIC), programmable logic arrays, cloud computing devices, and other hardware devices constructed to implement the methods described herein.

It should also be noted that the software implementations of the invention as described herein are optionally stored on a tangible storage medium, such as: a magnetic medium such as a disk or tape; a magneto-optical or optical medium such as a disk; or a solid state medium such as a memory card or other package that houses one or more read-only (non-volatile) memories, random access memories, or other re-writable (volatile) memories. A digital file attachment to email or other self-contained information archive or set of archives is considered a distribution medium equivalent to a tangible storage medium. Accordingly, the invention is considered to include a tangible storage medium or distribution medium, as listed herein and including art-recognized equivalents and successor media, in which the software implementations herein are stored.

Additionally, the various aspects of the disclosure may be implemented in a non-generic computer implementation. Moreover, the various aspects of the disclosure set forth herein improve the functioning of the system as is apparent from the disclosure hereof. Furthermore, the various aspects of the disclosure involve computer hardware that it specifically programmed to solve the complex problem addressed by the disclosure. Accordingly, the various aspects of the disclosure improve the functioning of the system overall in its specific implementation to perform the process set forth by the disclosure and as defined by the claims.

Aspects of the disclosure may include a server executing an instance of an application or software configured to accept requests from a client and giving responses accordingly. The server may run on any computer including dedicated computers. The computer may include at least one processing element, typically a central processing unit (CPU), and some form of memory. The processing element may carry out arithmetic and logic operations, and a sequencing and control unit may change the order of operations in response to stored information. The server may include peripheral devices that may allow information to be retrieved from an external source, and the result of operations saved and retrieved. The server may operate within a client-server architecture. The server may perform some tasks on behalf of clients. The clients may connect to the server through the network on a communication channel as defined herein. The server may use memory with error detection and correction, redundant disks, redundant power supplies and so on.

According to an example, the global navigation satellite system (GNSS) may include a device and/or system that may estimate its location based, at least in part, on signals received from space vehicles (SVs). In particular, such a device and/or system may obtain "pseudorange" measurements including approximations of distances between associated SVs and a navigation satellite receiver. In a particular example, such a pseudorange may be determined at a receiver that is capable of processing signals from one or more SVs as part of a Satellite Positioning System (SPS). Such an SPS may comprise, for example, a Global Positioning System (GPS), Galileo, Glonass, to name a few, or any SPS developed in the future. To determine its location, a satellite navigation receiver may obtain pseudorange measurements to three or more satellites as well as their positions at time of transmitting. Knowing the SV orbital parameters, these positions can be calculated for any point in time. A pseudorange measurement may then be determined based, at least in part, on the time a signal travels from an SV to the receiver, multiplied by the speed of light. While techniques described herein may be provided as implementations of location determination in GPS and/or Galileo types of SPS as specific illustrations according to particular examples, it should be understood that these techniques may also apply to other types of SPS, and that claimed subject matter is not limited in this respect.

Aspects of the disclosure may be web-based. For example, a server may operate a web application in conjunction with a database. The web application may be hosted in a browser-controlled environment (e.g., a Java applet and/or the like), coded in a browser-supported language (e.g., JavaScript combined with a browser-rendered markup language (e.g., Hyper Text Markup Language (HTML) and/or the like)) and/or the like such that any computer running a common web browser (e.g., Internet Explorer™, Firefox™, Chrome™, Safari™ or the like) may render the application executable. A web-based service may be more beneficial due to the ubiquity of web browsers and the convenience of using a web browser as a client (i.e., thin client). Further, with inherent support for cross-platform compatibility, the web application may be maintained and updated without distributing and installing software on each.

The many features and advantages of the invention are apparent from the detailed specification, and, thus, it is intended by the appended claims to cover all such features and advantages of the invention which fall within the true spirit and scope of the invention. Further, since numerous modifications and variations will readily occur to those skilled in the art, it is not desired to limit the invention to the exact construction and operation illustrated and described, and, accordingly, all suitable modifications and equivalents may be resorted to that fall within the scope of the invention.

The invention claimed is:

1. A system for detecting oil quality comprising:
a light source configured to generate light within an oil in an oil container;
the light source having an output that is located within the oil of the oil container;
a light sensor configured to detect the light from the light source after it has traversed through the oil in the oil container and generate an output signal based on a detected light;
the light sensor having an input that is located within the oil of the oil container;
a monitor configured to receive the output signal from the light sensor and determine an oil quality of the oil in the oil container and determine whether the oil quality exceeds discrete limits; and
an output configured to communicate the oil quality determined by the monitor at least when the oil quality exceeds discrete limits.

2. The system according to claim 1 wherein the light source is arranged in the oil container and the light source is submerged within the oil of the oil container.

3. The system according to claim 1 wherein the light sensor is arranged in the oil container and the light sensor is submerged within the oil of the oil container.

4. The system according to claim 1 further comprising a contact arranged in the oil to receive and reflect the light from the light source to the light sensor;
the contact having physical properties that are configured to provide reflection of the light from the light source to the light sensor; and
the physical properties of the contact are configured to change based on a quality of the oil within the oil container.

5. The system according to claim 1 further comprising a fiber optic cable to guide the light from the light source into the oil container,
wherein one end of the fiber optic cable comprises the output that is located within the oil of the oil container;
wherein the light source is arranged outside of the oil container; and
wherein the fiber optic cable extends from the output that is located within the oil of the oil container to the light source is arranged outside of the oil container.

6. The system according to claim 1 further comprising a fiber optic cable to guide the light received from the light source from the oil container to the light sensor,
wherein one end of the fiber optic cable comprises the input that is located within the oil of the oil container;
wherein the light sensor is arranged outside of the oil container; and
wherein the fiber optic cable extends from the input that is located within the oil of the oil container to the light sensor that is arranged outside of the oil container.

7. The system according to claim 1 further comprising:
a first fiber optic cable to guide the light from the light source into the oil container, wherein the light source is arranged outside of the oil container; and
a second fiber optic cable to guide the light received from the light source from the oil container to the light sensor, wherein the light sensor is arranged outside of the oil container,
wherein one end of the first fiber optic cable comprises the output that is located within the oil of the oil container;
wherein the first fiber optic cable extends from the output that is located within the oil of the oil container to the light source that is arranged outside of the oil container,
wherein one end of the second fiber optic cable comprises the input that is located within the oil of the oil container; and
wherein the second fiber optic cable extends from the input that is located within the oil of the oil container to the light sensor that is arranged outside of the oil container.

8. The system according to claim 1 further comprising:
a contact arranged in the oil to receive and reflect the light from the light source to the light sensor;
the contact having physical properties that are configured to provide reflection of the light from the light source to the light sensor;
the physical properties of the contact are configured to change based on a quality of the oil within the oil container;
a first fiber optic cable to guide the light from the light source into the oil container, wherein the light source is arranged outside of the oil container; and
a second fiber optic cable to guide the light received from the light source from the oil container to the light sensor, wherein the light sensor is arranged outside of the oil container,
wherein one end of the first fiber optic cable comprises the output that is located within the oil of the oil container;
wherein the first fiber optic cable extends from the output that is located within the oil of the oil container to the light source that is arranged outside of the oil container,
wherein one end of the second fiber optic cable comprises the input that is located within the oil of the oil container; and wherein the second fiber optic cable extends from the input that is located within the oil of the oil container to the light sensor that is arranged outside of the oil container.

9. The system according to claim 1 further comprising:
a microprocessor configured to at least one of the following: determine data regarding the oil quality, determine a location of the oil container, determine a status of the monitor, determine problems with the oil quality and/or the monitor, and determine recommended next steps and additional testing based on a determined oil quality;
a sensor input configured to receive data from the light sensor;
a light controller configured to control the light source; and
a memory configured to store the data regarding the oil quality, the location of the oil container, the status of the monitor, the problems with the oil quality and/or the monitor, and the recommended next steps and additional testing based on a determined oil quality.

10. The system according to claim 9 further comprising:
a communication device configured to wirelessly communicate the following to a server for storage in a database: data regarding the oil quality, the location of the oil container, a status of the monitor, problems with the oil quality and/or the monitor, and recommended next steps and additional testing based on the determined oil quality.

11. A process for detecting oil quality comprising:
generating within an oil in an oil container a light with a light source;
the light source having an output that is located within the oil of the oil container;
detecting the light from the light source after it has traversed through the oil in the oil container and generating an output signal based on a detected light with a light sensor;
receiving the output signal from the light sensor and determining an oil quality of the oil in the oil container and determining whether the oil quality exceeds discrete limits;
the light sensor having an input that is located within the oil of the oil container; and
communicating the oil quality determined by the monitor at least when the oil quality exceeds discrete limits with an output.

12. The process according to claim 11 wherein the light source is arranged in the oil container and the light source is submerged within the oil of the oil container.

13. The process according to claim 11 wherein the light sensor is arranged in the oil container and the light sensor is submerged within the oil of the oil container.

14. The process according to claim 11 further comprising arranging a contact in the oil to receive and reflect the light from the light source to the light sensor;
the contact having physical properties that are configured to provide reflection of the light from the light source to the light sensor; and
the physical properties of the contact are configured to change based on a quality of the oil within the oil container.

15. The process according to claim 11 further comprising arranging a fiber optic cable to guide the light from the light source into the oil container,
wherein one end of the fiber optic cable comprises the output that is located within the oil of the oil container;
wherein the light source is arranged outside of the oil container; and
wherein the fiber optic cable extends from the output that is located within the oil of the oil container to the light source that is arranged outside of the oil container.

16. The process according to claim 11 further comprising arranging a fiber optic cable to guide the light received from the light source from the oil container to the light sensor,
wherein one end of the fiber optic cable comprises the input that is located within the oil of the oil container;
wherein the light sensor is arranged outside of the oil container; and
wherein the fiber optic cable extends from the input that is located within the oil of the oil container to the light sensor is arranged outside of the oil container.

17. The process according to claim 11 further comprising:
arranging a first fiber optic cable to guide the light from the light source into the oil container, wherein the light source is arranged outside of the oil container; and
arranging a second fiber optic cable to guide the light received from the light source from the oil container to the light sensor, wherein the light sensor is arranged outside of the oil container,
wherein one end of the first fiber optic cable comprises the output that is located within the oil of the oil container;
wherein the first fiber optic cable extends from the output that is located within the oil of the oil container to the light source that is arranged outside of the oil container,
wherein one end of the second fiber optic cable comprises the input that is located within the oil of the oil container; and
wherein the second fiber optic cable extends from the input that is located within the oil of the oil container to the light sensor that is arranged outside of the oil container.

18. The process according to claim 11 further comprising:
arranging a contact in the oil to receive and reflect the light from the light source to the light sensor;
the contact having physical properties that are configured to provide reflection of the light from the light source to the light sensor;
the physical properties of the contact are configured to change based on a quality of the oil within the oil container;
arranging a first fiber optic cable to guide the light from the light source into the oil container, wherein the light source is arranged outside of the oil container; and
arranging a second fiber optic cable to guide the light received from the light source from the oil container to the light sensor, wherein the light sensor is arranged outside of the oil container,
wherein one end of the first fiber optic cable comprises the output that is located within the oil of the oil container;
wherein the first fiber optic cable extends from the output that is located within the oil of the oil container to the light source that is arranged outside of the oil container,
wherein one end of the second fiber optic cable comprises the input that is located within the oil of the oil container; and
wherein the second fiber optic cable extends from the input that is located within the oil of the oil container to the light sensor that is arranged outside of the oil container.

19. The process according to claim 11 further comprising:
determining with a microprocessor at least one of the following: data regarding the oil quality, a location of the oil container, a status of the monitor, problems with the oil quality and/or monitor, and recommended next steps and additional testing based on a determined oil quality;

receiving data from the light sensor from a sensor input;

controlling the light source with a light controller; and storing in a memory the data regarding the oil quality, the location of the oil container, the status of the monitor, the problems with the oil quality and/or the monitor, and the recommended next steps and additional testing based on a determined oil quality.

20. The process according to claim 19 further comprising wirelessly communicating with the monitor at least one of the following to a server for storage in a database: data regarding the oil quality, the location of the oil container, the status of the monitor, the problems with the oil quality and/or monitor, and the recommended next steps and additional testing based on the determined oil quality.

* * * * *